(12) United States Patent
Marple

(10) Patent No.: US 10,319,991 B2
(45) Date of Patent: Jun. 11, 2019

(54) ZINC ANODE COMPOSITION

(71) Applicant: Energizer Brands, LLC, St. Louis, MO (US)

(72) Inventor: Jack W. Marple, Avon, OH (US)

(73) Assignee: Energizer Brands, LLC, St. Louis, MO (US)

( * ) Notice: Subject to any disclaimer, the term of this patent is extended or adjusted under 35 U.S.C. 154(b) by 13 days.

(21) Appl. No.: 15/521,223

(22) PCT Filed: Oct. 23, 2015

(86) PCT No.: PCT/US2015/057063
§ 371 (c)(1),
(2) Date: Apr. 21, 2017

(87) PCT Pub. No.: WO2016/065230
PCT Pub. Date: Apr. 28, 2016

(65) Prior Publication Data
US 2017/0358793 A1 Dec. 14, 2017

Related U.S. Application Data

(60) Provisional application No. 62/067,756, filed on Oct. 23, 2014.

(51) Int. Cl.
*H01M 4/24* (2006.01)
*H01M 4/58* (2010.01)
(Continued)

(52) U.S. Cl.
CPC ......... *H01M 4/244* (2013.01); *H01M 4/5825* (2013.01); *H01M 4/62* (2013.01);
(Continued)

(58) Field of Classification Search
CPC ...... H01M 4/244; H01M 4/5825; H01M 4/62; H01M 4/621; H01M 10/052
(Continued)

(56) References Cited

U.S. PATENT DOCUMENTS 4,195,120 A 3/1980 Rossler et al.
4,777,100 A 10/1988 Chalilpoyil et al.
(Continued)

FOREIGN PATENT DOCUMENTS

AU 2005225138 A1 5/2006
AU 2004210507 B2 10/2009
(Continued)

OTHER PUBLICATIONS

BASF, "Kollicoat IR: Polyvinyl alcohol-polyethylene glycol graft copolymer for instant-release coatings and quick-dissolving formulations", BASF Technical Information, Feb. 2013, 14 pages, retrieved from <https://www.google.com/?gws_rd=ssl#q=kollicoat+ir+technical+information+basf+2013> on Jan. 14, 2017.
(Continued)

*Primary Examiner* — Amanda C. Walke
(74) *Attorney, Agent, or Firm* — Alston & Bird LLP

(57) ABSTRACT

An alkaline electrochemical cell, preferably a zinc/air cell which includes a container; a negative electrode, a positive electrode, wherein said negative electrode and said positive electrode are disposed within the container, and an alkaline electrolyte, wherein the negative electrode comprises zinc, a branched chain fluorosurfactant, barium sulfate (and, more specifically, amino- and/or epoxy-functionalized barium sulfate) and nano sized zinc oxide. The negative electrode composition supports high zinc to electrolyte weight ratios.

18 Claims, 10 Drawing Sheets

(51) Int. Cl.

| | |
|---|---|
| *H01M 4/62* | (2006.01) |
| *C01G 9/02* | (2006.01) |
| *C07C 69/34* | (2006.01) |
| *C07C 69/63* | (2006.01) |
| *H01M 12/06* | (2006.01) |

(52) U.S. Cl.
CPC ............... *C01G 9/02* (2013.01); *C07C 69/34* (2013.01); *C07C 69/63* (2013.01); *H01M 12/06* (2013.01)

(58) Field of Classification Search
USPC ........................................................ 429/231
See application file for complete search history.

(56) References Cited

U.S. PATENT DOCUMENTS

| | | | |
|---|---|---|---|
| 5,300,394 | A | 4/1994 | Miller et al. |
| 5,312,476 | A | 5/1994 | Uemura et al. |
| 5,378,562 | A | 1/1995 | Passaniti et al. |
| 5,401,590 | A | 3/1995 | Chalilpoyil et al. |
| 5,419,977 | A | 5/1995 | Weiss |
| 5,464,709 | A | 11/1995 | Getz et al. |
| 5,677,084 | A | 10/1997 | Tsukamoto et al. |
| 6,203,943 | B1 | 3/2001 | Bennett et al. |
| 6,551,742 | B1 | 4/2003 | Huq et al. |
| 6,602,629 | B1 | 8/2003 | Guo et al. |
| 6,780,347 | B2 | 8/2004 | Ndzebet |
| 6,872,489 | B2 | 3/2005 | Armacanqui et al. |
| 6,939,630 | B2 | 9/2005 | Sotomura et al. |
| 6,967,038 | B2 | 11/2005 | O'Brien |
| 7,005,213 | B2 | 2/2006 | Ndzebet et al. |
| 7,008,723 | B2 | 3/2006 | Daniel-Ivad et al. |
| 7,208,248 | B2 | 4/2007 | Hayashi et al. |
| 7,563,537 | B2 | 7/2009 | Pratt et al. |
| 7,615,508 | B2 | 11/2009 | Kaplan et al. |
| 7,754,381 | B2 | 7/2010 | Fujino et al. |
| 7,993,508 | B2 | 8/2011 | Stimits et al. |
| 8,586,244 | B2 | 11/2013 | Fensore et al. |
| 8,652,685 | B2 | 2/2014 | Guo |
| 8,945,736 | B2 | 2/2015 | Uensel et al. |
| 8,999,874 | B2 | 4/2015 | Kishimoto et al. |
| 9,136,540 | B2 | 9/2015 | Padhi et al. |
| 2004/0229107 | A1 | 11/2004 | Smedley |
| 2005/0123833 | A1 | 6/2005 | Schubert et al. |
| 2005/0287438 | A1* | 12/2005 | Bernard ................ H01M 4/624 429/223 |
| 2006/0068288 | A1 | 3/2006 | Johnson |
| 2007/0048576 | A1 | 3/2007 | McKenzie et al. |
| 2007/0092429 | A1 | 4/2007 | Mao et al. |
| 2007/0122699 | A1 | 5/2007 | Pratt |
| 2007/0154704 | A1 | 7/2007 | Debergalis et al. |
| 2007/0160898 | A1 | 7/2007 | Takamura et al. |
| 2008/0096074 | A1 | 4/2008 | Wu |
| 2008/0155813 | A1 | 7/2008 | Dopp et al. |
| 2008/0241683 | A1 | 10/2008 | Fensore |
| 2009/0320718 | A1 | 12/2009 | Hierse et al. |
| 2011/0033747 | A1 | 2/2011 | Phillips et al. |
| 2011/0143253 | A1 | 6/2011 | Miyata et al. |
| 2011/0265669 | A1 | 11/2011 | Padberg |
| 2011/0287305 | A1* | 11/2011 | Scordilis-Kelley ......................... H01M 2/1653 429/163 |
| 2012/0111233 | A1 | 5/2012 | Hierse et al. |
| 2013/0162216 | A1 | 6/2013 | Zhamu |
| 2014/0099539 | A1* | 4/2014 | Yamazaki ............. H01M 4/386 429/211 |
| 2014/0170478 | A1* | 6/2014 | Liao .................. H01M 10/0525 429/199 |
| 2014/0239239 | A1* | 8/2014 | Cha ...................... H01M 4/622 252/519.33 |
| 2015/0244000 | A1 | 8/2015 | Ozaki et al. |
| 2017/0012317 | A1* | 1/2017 | Fukuta ................. H01M 4/485 |
| 2017/0237133 | A1* | 8/2017 | Marple ............... H01M 4/8875 429/406 |

FOREIGN PATENT DOCUMENTS

| | | | |
|---|---|---|---|
| CA | 2216823 | A1 | 3/1998 |
| CA | 2716012 | A1 | 10/2009 |
| CA | 2321313 | C | 12/2009 |
| CA | 2795492 | A1 | 10/2011 |
| CA | 2472557 | C | 12/2014 |
| DE | 102006031143 | A1 | 1/2008 |
| EP | 2053674 | B1 | 12/2012 |
| EP | 2654107 | A1 | 10/2013 |
| WO | WO 2003/052843 | A2 | 6/2003 |
| WO | WO 2008/051508 | A2 | 5/2008 |
| WO | WO 2009/016521 | A2 | 2/2009 |

OTHER PUBLICATIONS

Toon, John, "Smart Hydrogel Coating Creates "Stick-slip" Control of Capillary Action", Georgia Tech News Center, Jul. 27, 2015, 5 pages, retrieved from <http://www.news.gatech.edu/2015/07/25/smart-hydrogel-coating-creates-%E2%80%9Cstick-slip%E2%80%9D-control-capillary-action> on Jan. 14, 2017.

Pfeffer, R., "Synthesis of Engineered Particulates With Tailored Properties Using Dry Particle Coating," Powder Technology, vol. 117, 2001, pp. 40-67.

Yang, J., "Dry Particle Coating for Improving the Flowability of Cohesive Powders," Powder Technology, vol. 158, 2005, pp. 21-33.

Neburchilov, V., "A Review on Air Cathodes for Zinc-Air Fuel Cells," Journal of Power Source, vol. 195, 2010, pp. 1271-1291.

Pund, K., "Recovery Act: Nanoengineered Ultracapacitor Material Surpasses the $/kW Threshold for Use in EDV' s," EnerG2, May 16, 2012. http://www1.eere.energy.gov/vehiclesandfuels/pdfs/merit_review_2012/energy_storage/arravt011_es_pund_2012_p.pdf.

ENERG2 Press Release "EnerG2 nano-structured hard carbon boosts Li-ion anode capacity by >50% compared to standard graphite," Mar. 27, 2013, http://www.greencarcongress.com/2013/03/energ2-20130327.html.

International Searching Authority, International Search Report and Written Opinion for International Application No. PCT/US2015/054489, dated Dec. 29, 2015, 8 pages, United States Patent and Trademark Office.

The International Bureau of WIPO, International Preliminary Report on Patentability (Chapter I) for International Application No. PCT/US2015/054489, dated Apr. 11, 2017, 7 pages, Switzerland.

International Searching Authority, International Search Report and Written Opinion for International Application No. PCT/US2015/057063, dated Jan. 22, 2016, 6 pages, United States Patent and Trademark Office.

Schellenberger, Steffen, et al., "A New Generation of High-Speed Fluorosurfactants", *PCI Magazine*, May 1, 2013 (previously published in European Coatings Journal on Nov. 2012), 7 pages, retrieved from < http://www.pcimag.com/articles/97759-a-new-generation-of-high-speed-fluorosurfactants > on Mar. 9, 2017.

Usui, Hiroyuki, et al., "Novel Composite Thick-Film Electrodes Consisted of Zinc Oxide and Silicon for Lithium-Ion Battery Anode", *International Journal of Electrochemical Science*, May 1, 2012, pp. 4322-4334, vol. 7, retrieved from < Novel Composite Thick-Film Electrodes Consisted of Zinc Oxide and Silicon for Lithium-Ion Battery Anode > on Apr. 19, 2017.

U.S. Appl. No. 15/516,811, Non-Final Office Action dated Jul. 27, 2018.

* cited by examiner

Improved zinc input capacity while maintaining IEC performance

AZ13 Control Discharge Profile

AZ13 with Sachtoperse AM

AZ13 with Sachtoperse EP comparison of control to recommended anode formulation changes NAF with nano ZnO vs. Control Improved operating voltage and end of life AZ13 Performance as a Function of Application Drain Rate and Anode Void Volume. From Top to Bottom: 3mA, IEC-HR, and wireless AZ312 discharged at 2mA control in black upper graph control, lower graph based on anode formulation changes

ZINC ANODE COMPOSITION

CROSS REFERENCE TO RELATED APPLICATIONS

This application is a National Stage Application, filed under 35 U.S.C. 371, of International Application No. PCT/US2015/057063, filed Oct. 23, 2015, which claims priority to U.S. Application No. 62/067,756, filed Oct. 23, 2014; the contents of both of which are hereby incorporated by reference in their entirety.

BACKGROUND

Related Field

With respect to United States Application No. PCT/US15/54489 filed on Oct. 7, 2015, this application is a continuation-in-part of that application and, in any event, incorporated herein by reference in its entirety in any applicable jurisdictions where such designation and action are possible.

The present invention relates to a negative electrode of an alkaline zinc air electrochemical cell. The negative electrode includes zinc as an active material and further includes a hydrogen gas inhibiting surfactant, a functionalized barium sulfate and nano-sized zinc oxide. More particularly, the invention discloses an alkaline electrochemical cell that is capable of providing improved service when utilized by high drain devices.

Description of Related Art

The alkaline zinc air cell system is particularly sensitive to zinc stability and low gassing rates. Any buildup of either hydraulic or pneumatic pressure within the anode compartment can result in failure of the air electrode as electrolyte is forced into the critical solid-gas-liquid reaction sites. Excessive electrolyte within the air electrode further leads to a decrease in its tensile strength, which can result in a higher resistance in the electrode to can contact as well as an oxygen diffusion barrier film at the PFTE membrane to electrode interface. This is typically observed as a sloping end of life discharge as polarization increases from lack of effective oxygen available for reduction within the air electrode matrix.

Battery manufacturers are expected to continually increase the quality and performance of their battery products. It is desired to increase the service delivered for all cell sizes and while the AZ13 zinc air cell is used in the illustrating examples, the invention presented can be applied to other cell sizes and alkaline batteries. Cell capacity is determined by zinc input and zinc efficiency. Cell designers can use a zinc to electrolyte ratio to adjust zinc input and adjust anode compositions to optimize anode utilization/efficiency. In addition, performance can be increased by optimizing the cell's end of life behavior. Cell gassing also plays into overall cell performance as it can factor into a cell's end of life. Electrode deformation and doming caused by internal pressure can take away from anode volume, and negatively affect the air electrode performance. In order to achieve a service level increase, it will be a requirement to increase the amount of zinc in the cell by increasing the zinc to electrolyte ratio while also decreasing electrode dome and maintaining or increasing electrode efficiencies.

The alkaline battery industry has a long history of defining anode additives, with the intent of stabilize or minimizing zinc corrosion. This is particularly true since the elimination of mercury from alkaline battery products. For the most part, corrosion has been controlled through the addition of surfactants also referred to as wetting and dispersing additives. Identifying and qualifying new additives is challenging since it is not the intent of the manufacturers of these surfactants that they be used as film formers on the surface of zinc or at zinc grain boundaries, or minimizing the reaction of water and zinc, particularly with high surface area zinc alloys. The selection of the preferred additive is further complicated by the fact that different zinc based chemistries, cell form factors, application drains, shelf life claims, sensitivities to gas generation, and anode processing differences such as gels and powdered forms has led to a wide variation in specifications. Surfactants and dispersion aids can serve more than one function. Some additives are used primarily to influence rheology properties while possessing a secondary effect of reducing zinc corrosion.

U.S. Pat. No. 4,777,100 relates to reportedly reducing corrosion in aqueous electrochemical cells having zinc anodes comprised of single crystal zinc particles by the addition of small amounts of a gas inhibiting surfactant, for example, an organic phosphate inhibitor such as RA600 from GAF Corp. to the cell. A synergistically lowered rate of corrosion and cell gassing is reportedly obtained even with reduction of mercury content.

U.S. Pat. No. 5,401,590 relates to a method for inhibiting the occurrence of load voltage instability in zinc anodic alkaline cells. The anode active material contains a gelled slurry of zinc alloy particles, a gelling agent, an aqueous alkaline solution and a mixed surfactant containing an anionic surfactant and a nonionic surfactant. The gelled anode active material reportedly inhibits the occurrence of load voltage instability and reportedly simultaneously reduces hydrogen evolution even though the cell contains no added amounts of mercury.

U.S. Pat. No. 6,551,742 relates to an anionic fluorosurfactant, such as an anionic fluoroaliphaticcarboxylate, can be added to the anode mixture of a zinc/air cell. The addition of the surfactant and a heat treated anode casing eliminates the need to add mercury to the anode material.

U.S. Pat. No. 6,872,489 discloses a sulfonic acid type organic surfactant which is incorporated into the gelled anode of an alkaline electrochemical cell, optionally with an organic phosphate ester surfactant. When the two surfactants are provided in a gelled anode in combination, discharge leakage is reportedly reduced and gel gassing is reportedly suppressed relative to that of gels lacking both surfactants. Additionally, cell discharge performance is reportedly improved relative to that of cells lacking both surfactant additives.

U.S. Pat. No. 7,008,723 relates to a method of manufacturing an anode composition for use in an electrochemical cell, in which the anode comprises an electrochemically active material, the method comprising the steps of mixing the electrochemically active material with an alkaline electrolyte solution, an organic surfactant, an indium compound, and a gelling agent, such that the indium compound or a portion thereof is added in an alkaline environment.

U.S. Pat. No. 7,993,508 discloses an alkaline zinc air cell that contains either a surfactant Carbowax c 550, or a surfactant Disperbyk r D102.

U.S. Pat. No. 8,586,244 relates to electrochemical cells wherein the negative electrode includes zinc as an active material and further includes a reported synergistic combination of a solid zinc oxide and a surfactant.

WO 2003052843 A2 relates to an alkaline electrochemical cell that contains an oxazoline surfactant additive.

BRIEF SUMMARY

According to a first aspect of the present invention, an embodiment of the invention can include any one or a combination of the following features: An alkaline electrochemical cell, comprising a container; a negative electrode, a positive electrode, wherein the negative electrode and the positive electrode are disposed within the container and, a separator located between the negative electrode and the positive electrode, and an alkaline electrolyte, wherein the negative electrode comprises zinc, and a sulfotricarballylate surfactant. The sulfotricarballylate surfactant is a fluorosurfactant is of the formula (I)

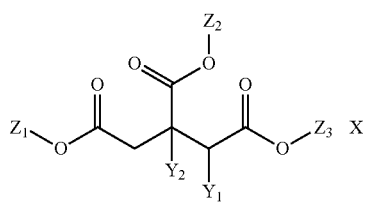

where the groups $Z_i$ ($Z_1$, $Z_2$, and $Z_3$) are, independently of one another, branched or unbranched alkyl groups or groups of the structure $R_f(A(CR_1R_2)_{ci}$—$(CR_3R_4)_{c'i})_{di}$—, where the respective indices ci and c'i are, independently of one another, 0-10, and di=0-5, where $R_f$ is a branched or unbranched, fluorine-containing alkyl radical, $R_1$ to $R_4$ are, independently of one another, hydrogen or a branched or unbranched alkyl group, ci and c'i are not simultaneously 0, and A=O, S and/or N. $Y_1$ is an anionic polar group and $Y_2$ is a hydrogen atom, or vice versa, X is a cation, and at least one of the groups $Z_i$ is a group of the structure $R_f(A(CR_1R_2)_{ci}$—$(CR_3R_4)_{c'i})_{di}$—. The sulfotricarballylates surfactant preferably has a molecular weight of about between 800 and 1320.

In another embodiment, the sulfotricarballylate surfactant included to suppress corrosion of the zinc in the negative electrode of the alkaline cell is characterized by the formula (Ia)

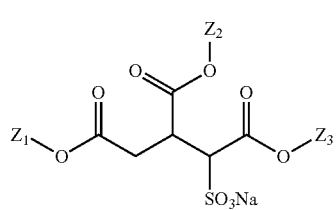

and where Z1=Z2=Z3=F3C(CF2) ai(CH2) bi(O(CH2) ci)di-, where ai=1-2, bi=1-2, ci=2, di=1-3, Y1 or Y2 is a sulfonate group —SO3-, and X=Na+. Alternatively, Z1=Z2=Z3=F3C(CF2)(CH2)(O(CH2CHCH2CH3)).

In the embodiment, the sulfotricarballylates contains more than one fluorinated end groups, and all of the fluorinated end groups can be identical. Preferably the sulfotricarballylate surfactant comprises three fluorinated end groups. Each fluorinated end group can include a fluorinated carbon chain such as F3C(CF2)2 and F3C(CF2). In the embodiment wherein the sulfotricarballylate surfactant comprises three fluorinated end groups, each end group can comprise such a fluorinated carbon chain.

The sulfotricarballylates surfactant is in the form of a mixture, and added so as to be present in the cell in an amount from 10 to 1000 ppm based on the total weight of the zinc. Preferably the concentration of the sulfotricarballylate in the cell is present in an amount from 10 to 200 ppm, or 10 to 100 ppm based on the total weight of the zinc, and most preferably in an amount from 10 to 40 ppm based on the total weight of the zinc. When added to the negative electrode of the alkaline electrochemical cell the sulfotricarballylate surfactant can form a monolayer on the surface of the zinc so as to inhibit corrosion of the zinc.

In an embodiment the alkaline electrochemical cell can comprise: a container; a negative electrode, a positive electrode, wherein said negative electrode and said positive electrode are disposed within the container, and an alkaline electrolyte, wherein the negative electrode comprises zinc, and barium sulfate. Preferably the barium sulfate is functionalized. When the barium sulfate is functionalized, the functional groups may be amino groups, epoxide groups and combinations thereof. The barium sulfate should be provided at a concentration no greater than 0.2 weight percent of the overall anode mixture.

The electrochemical cell's negative electrode can further comprises a fluorosurfactant, preferably a sulfotricarballylate, and zinc oxide. Preferably the zinc oxide is nano-sized. This negative electrode composition enables a weight ratio of zinc to electrolyte of greater than 3.6, and enables improved performance in the cell.

These and other features, advantages, and objects of the present invention will be further understood and appreciated by those skilled in the art by reference to the following specification, claims, and appended drawings. While specific embodiments are described in the preceding paragraphs, it will be understood that features specific to one embodiment may be used in combination with or in place of features described for different embodiments.

DETAILED DESCRIPTION OF VARIOUS EMBODIMENTS

Figure 1:
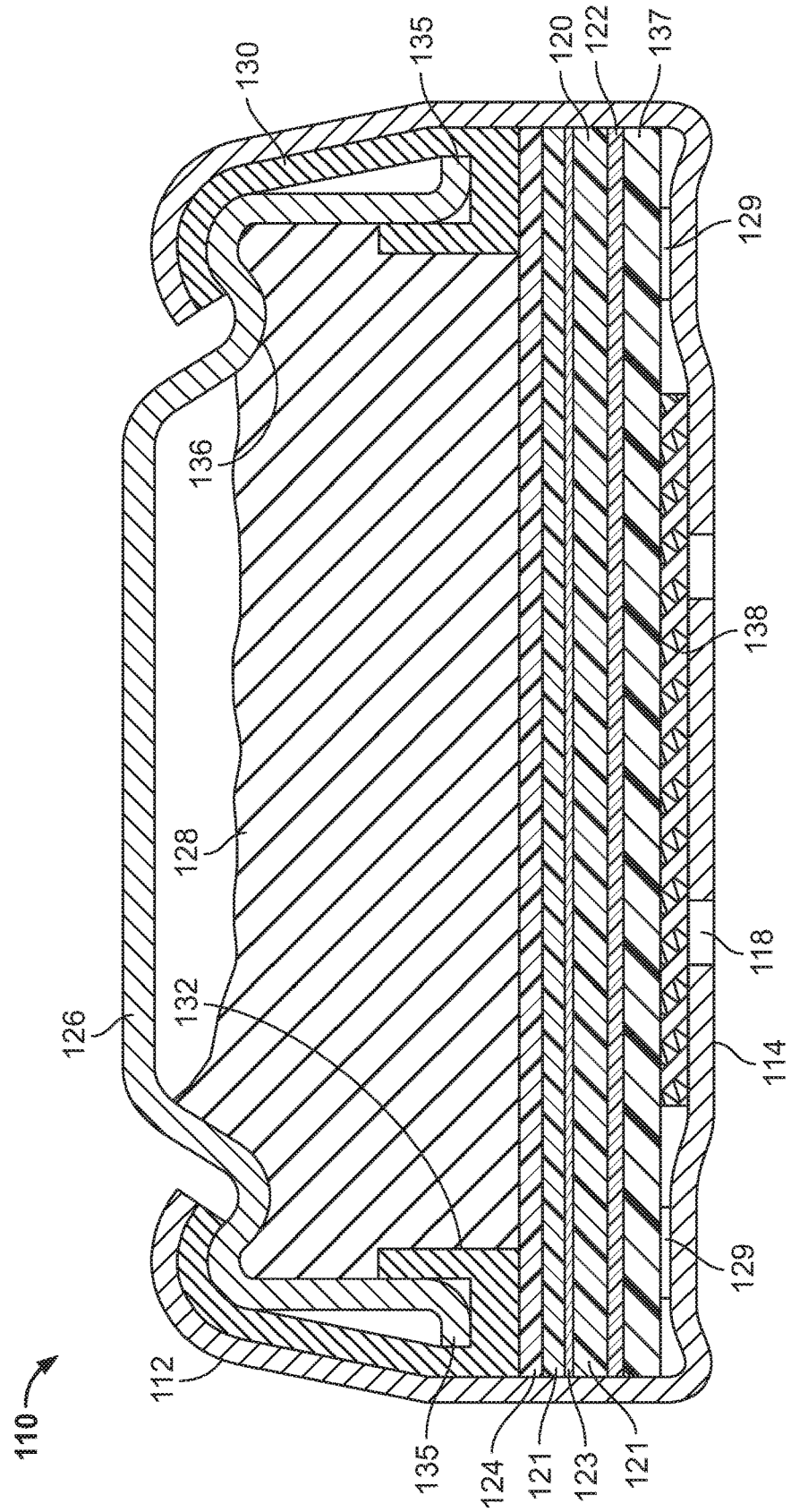
FIG. 1 is an elevational view, in cross-section, of a metal-air cell with a catalytic electrode.

As shown in an example of an electrochemical cell according to the invention is shown in FIG. 1. The cell 110 can include a cathode casing 112 and an anode casing 126. At least one aperture 118 is present in the cathode casing 112 to act as an air or oxygen entry port. A catalytic positive electrode (such as an air electrode) 120 is disposed near the aperture 118 in the cathode casing 112. The catalytic electrode 120 can include a catalytic layer containing a mixture of carbon, a catalyst, and a binder. Catalytic electrode 120 preferably has a barrier layer 122 laminated thereon. The barrier layer 122 can be laminated on the side of the catalytic electrode closest to the aperture 118 cell. Catalytic electrode 120 can contain an electrically conductive current collector 123 embedded therein, preferably on the side of the electrode opposite the barrier layer 122. The cell 110 may optionally contain a second barrier layer 137 between the first barrier layer 122 and central region 114 of the surface of the cathode casing 112 containing the aperture 118. The barrier layers 122, 137 have a low enough surface tension to be resistant to wetting by electrolyte, yet porous enough to allow oxygen to enter the electrode at a rate sufficient to support the desired maximum cell reaction rate. At least one layer of separator 124 is positioned on the side of the catalytic electrode 120 facing the anode 128. The separator 124 is iconically conductive and electrically nonconductive. The total thickness of the separator 124 is preferably thin to minimize its volume, but must be thick and strong enough to prevent short circuits between the anode 128 and catalytic electrode 120. The separator 124 can be adhered to the surface of the catalytic electrode 120 to provide good ion transport between the electrodes and to prevent the formation of gas pockets between the catalytic electrode 120 and the separator 124. Similarly, adjacent layers of the separator 124 can be adhered to each other. A layer of porous material 138 can be positioned between catalytic electrode 120 and the surface of casing 112 to evenly distribute oxygen to electrode 120. A sealant 129 can be used to bond portions of the catalytic electrode 120 to the cathode casing 112. The anode casing 126 can have a rim 135 that is flared outward at its open end. Alternatively, a cell can essentially straight side walls with little or no outward flare or a rim that is folded outward and back along the side wall to form a substantially U-shaped side wall with a rounded edge at the open end of the casing. The anode casing 126 can have an inner surface 136 in contact with the anode mixture 128 and electrolyte. Cell 110 can includes a gasket 130, made from an elastomeric material for example, to provide a seal between the cathode casing 112 and anode casing 126. The bottom edge of the gasket 130 can be formed to create an inwardly facing lip 132, which abuts the rim of anode casing 126. Optionally, a sealant may be applied to the sealing surfaces of the gasket 130, cathode casing 112 and/or anode casing 126. A suitable tab (not shown) can be placed over the openings 118 until the cell 110 is ready for use, to keep air from entering the cell 110 before use.

A catalytic layer 121 contains a catalytic composition that includes composite particles comprising nano-catalyst particles adhered to (e.g., adsorbed onto) the external and internal surfaces (including surfaces of open pores) of highly porous carbon substrate particles.

Examples of zinc air cell cathode construction that can be used in conjunction with the present invention are disclosed in U.S. Patent Application Publication No. 2008/0155813 A1.

The anode casing 126 forms the top of the cell and has a rim 135 which is flared outward at its open end. Alternatively, a cell can have a refold anode casing in which the rim is folded outward and back along the side wall to form a substantially U-shaped side wall with a rounded edge at the open end of the casing, or the anode casing can have essentially straight side walls and that has a rim with little or no outward flare.

The anode casing 126 can be formed from a substrate including a material having a sufficient mechanical strength for the intended use such as stainless steel, mild steel, cold rolled steel, aluminum, titanium or copper. Preferably the anode casing includes one or more additional layers of material to provide good electrical contact to the exterior surface of the anode casing 126, resistance of the external surface to corrosion, and resistance to internal cell gassing where the internal surface of the anode casing 126 comes in contact with the anode 128 or electrolyte. Each additional layer can be a metal such as nickel, tin, copper, or indium, or a combination or alloy thereof, and layers can be of the same or different metals or alloys. Examples of plated substrates include nickel plated steel, nickel plated mild steel and nickel plated stainless steel. Examples of clad materials (i.e., laminar materials with at least one layer of metal bonded to another layer of metal) include, as listed in order from an outer layer to an inner layer, two-layered (biclad) materials such as stainless steel/copper, three-layered (triclad) materials such as nickel/stainless steel/copper and nickel/mild steel/nickel, and materials with more than three clad layers.

The anode casing 126 can include a layer that is post-plated (i.e., plated after forming the anode casing into its desired shape). The post-plated layer is preferably a layer of metal with a high hydrogen overvoltage to minimize hydrogen gassing within the cell 110. Examples of such metals are copper, tin, zinc, indium and alloys thereof. A preferred metal is tin, and a preferred alloy is one comprising copper, tin and zinc.

Cell 110 also includes a gasket 130 made from an elastomeric material which serves as the seal. The bottom edge of the gasket 130 has been formed to create an inwardly facing lip 132, which abuts the rim of anode casing 126. Optionally, a sealant may be applied to the sealing surface of the gasket, cathode casing and/or anode casing. Suitable sealant materials will be recognized by one skilled in the art. Examples include asphalt, either alone or with elastomeric materials or ethylene vinyl acetate, aliphatic or fatty polyamides, and thermoplastic elastomers such as polyolefins, polyamine, polyethylene, polypropylene and polyisobutene.

During manufacture of the cell, anode casing 126 can be inverted, and then a negative electrode composition or anode mixture 128 and electrolyte put into anode casing 126. The anode mixture insertion can be a two-step process wherein dry anode mixture materials are dispensed first into the anode casing 126 followed by KOH solution dispensing. Alternatively, the wet and dry components of the anode mixture are preferably blended beforehand and then dispensed in one step into the anode casing 126. Electrolyte can creep or wick along the inner surface 136 of the anode casing 126, carrying with it materials contained in anode mixture 128 and/or the electrolyte. The amount of the electrolyte dispensed takes into account both the desired electrolyte to zinc ratio (a weight ratio) and the void volume desired within the cell.

An example of an anode mixture 128, for a button cell comprises a mixture of zinc, electrolyte, and organic compounds. The anode mixture 128 preferably includes zinc powder, a binder such as CARBOPOL® 940 or CARBOPOL® 934, and a gassing inhibitor such as indium hydroxide (In(OH)$_3$) in amounts of about 99.7 weight percent zinc, about 0.25 weight percent hinder, and about 0.045 weight percent indium hydroxide. CARBOPOL® 934 and CARBOPOL® 940 are acrylic acid polymers in the 100% acid form and are available from Noveon Inc. of Cleveland, Ohio. A preferred alternative gelling agent is SANFRESH™ DK-300 a sodium salt of an acrylic acid polymer available from Sanyo Chemical Industries Ltd., Kyoto, Japan.

The electrolyte composition for a button cell can be a mixture of about 97 weight percent potassium hydroxide (KOH) solution where the potassium hydroxide solution is 28-40 weight percent, preferably 30-35 weight percent, and more preferably about 33 weight percent aqueous KOH solution, and about 1.00 to 3.00 weight percent zinc oxide (ZnO). Any specific whole integers between the stated ranges for potassium hydroxide weight percent are contemplated (e.g., 29, 34, 38, etc.), as are one tenth increments for weight percent zinc oxides (e.g., 1.10, 2.30, 2.70, etc.).

Nano zinc oxide can also be added to the anode and can provide advantages relative regular zinc oxide. It should be noted that nano zinc oxide is available from several sources today based on its use in paints. For example; Bruggemann Chemical, NanoPhase Technologies, and Grillo provide nano zinc oxide. Surface areas can range from 20 to 100 square meters per gram. Additional, more preferred upper limits includes 100, 90, 80, 70, 60, 50, 40 or 30 square meters per gram, whereas the lower limits may be 20, 30, 40, 50, 60, 70, 80 or 90 square meters per gram. These upper and lower limits may be paired in any combination (e.g., 20 to 70; 40 to 100; 70 to 80; etc.).

Preferred zinc powders are low-gassing zinc compositions suitable for use in alkaline cells with no added mercury. Examples are disclosed in U.S. Pat. No. 6,602,629 (Guo et al.), U.S. Pat. No. 5,464,709 (Getz et al.) and U.S. Pat. No. 5,312,476 (Llemura et al.), which are hereby incorporated by reference.

One example of a low-gassing zinc is ZCA grade 1230 zinc powder from Zinc Corporation of America, Monaca, Pa., which is a zinc alloy containing about 400 to about 550 parts per million (ppm) of lead. The zinc powder preferably contains a maximum of 1.5 (more preferably a maximum of 0.5) weight percent zinc oxide (ZnO). Furthermore, the zinc powder may have certain impurities. The impurities of chromium, iron, molybdenum, arsenic, antimony, and vanadium preferably total 25 ppm maximum based on the weight of zinc. Also, the impurities of chromium, iron, molybdenum, arsenic, antimony, vanadium, cadmium, copper, nickel, tin, and germanium preferably total no more than 68 ppm of the zinc powder composition by weight. More preferably, the zinc powder contains no more than the following amounts of iron, cadmium, copper, tin, chromium, nickel, molybdenum, arsenic, vanadium, antimony, and germanium, based on/the weight of zinc: Fe—3.0 ppm, Cd—8 ppm, Cu—8 ppm, Sn—1 ppm, Cr—1 ppm, Ni—1 ppm, Mo—0.25 ppm, As—0.1 ppm, Sb—0.2 ppm, V—1 ppm, and Ge—0.06 ppm. The lower preferred limit for each of the impurities identified in this paragraph would be as close to 0 ppm as is reasonably practical.

In another embodiment, the zinc powder preferably is a zinc alloy composition containing bismuth, indium and aluminum. The zinc alloy preferably contains about 100 ppm of bismuth, 200 ppm of indium, and 100 ppm of aluminum. The zinc alloy preferably contains a low level of lead, such as about 35 ppm or less. In a preferred embodiment, the average particle size ($D_{50}$) is about 90 to about 120 microns. Examples of suitable zinc alloys include product grades NGBIA 100, NGBIA 115, and BIA available from N.V. Umicore, S.A., Brussels, Belgium. The values stated for zinc alloy compositions are nominal, and other useful levels of alloys may be possible.

The selection of zinc additives, for corrosion control, can be very challenging. Since these additives are often surfactants and other agents which have interactions with other components, they can influence viscosity and rheology properties.

Surfactants form films on the zinc surface which impact cell impedance and rate capability, and can influence the solubility of ZnO. They are often extremely concentration dependent which further complicates their evaluation. Surfactants used in zinc air cell anode formulations such as Disperbyk 102 and Carbowax 550 are extremely concentration sensitive and have significant impact on front end rate capability and cell impedance. It is desired to use a zinc additive which forms a thin but dense film on the zinc surface and is robust to concentration effects above the monolayer requirement.

In order to find a zinc additive that provides a thin but dense film on the surface of zinc which effectively reduces corrosion without having a negative impact on cell impedance and high rate performance, a sulfotricarballylate which is a fluorosurfactant with short chain, branched fluorocarbon end groups and carboxylate acid anchor groups was used as a zinc additive in an alkaline zinc air cell. The sulfotricarballylate is available as Tivida L2300 from EMD Millipore, also known as Merck Millipore outside the United States and Canada.

A first embodiment relates to alkaline cells with zinc additive compounds of the formula (I).

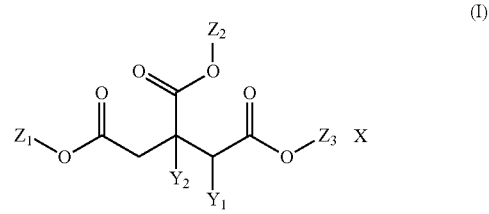

where the groups $Z_i$ ($Z_1$, $Z_2$, and $Z_3$) are, independently of one another, branched or unbranched alkyl groups or groups of the structure $R_f(A(CR_1R_2)_{ci}—(CR_3R_4)_{c'i})_{di}$—, where the respective indices ci and c'i are, independently of one another, 0-10, and di=0-5, where $R_f$ is a branched or unbranched, fluorine-containing alkyl radical, $R_1$ to $R_4$ are, independently of one another, hydrogen or a branched or unbranched alkyl group, ci and c'i are not simultaneously 0, and A=O, S and/or N, $Y_1$ is an anionic polar group and $Y_2$ is a hydrogen atom, or vice versa, X is a cation, and at least one of the groups $Z_i$ is a group of the structure $R_f(A(CR_1R_2)_{ci}—(CR_3R_4)_{c'i})_{di}$—. It is preferred for formula (I) that di>0 if $Z_1$, $Z_2$, and $Z_3$ are all a group of the structure $R_f(O(CH_2)_{c'i})_{di}$ and all $R_f$ are selected from $CF_3CF_2CH_2$—, $CF_3CF_2CH_2CH_2$—, $CF_3CF_2CF_2CH_2$— or $H(CF_2)_4CH_2$—.

The radicals $R_i$ are branched or unbranched, fluorine-containing alkyl groups. The radicals $R_i$ may be partly or perfluorinated and preferably contain terminal perfluorinated groups. Preference is given to branched or unbranched, fluorine-containing alkyl groups having 1 to 10 C atoms. Unbranched fluorine-containing alkyl groups preferably contain 1 to 6 C atoms, in particular 1-4 C atoms. Branched fluorine-containing alkyl groups preferably contain 3 to 6 C atoms, in particular 3-4 C atoms. The branched fluorine-containing alkyl groups used are preferably $(CF_3)_2$—CH— or $(CF_3)_3$—C— groups.

Another embodiment relates to alkaline cells with zinc additive compounds of the formula (Ia)

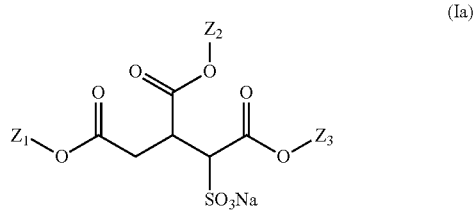

are, in particular, compounds in which all variables have the preferred meanings. Preference is explicitly given to compounds in which $Z_1=Z_2=Z_3=F_3C(CF_2)_{ai}(CH_2)_{bi}(O(CH_2)_{ci})_{di}$—, where ai=1-2, bi=1-2, ci=2, di=1-3, $Y_1$ or $Y_2$ is a sulfonate group —$SO_3^-$, and X=$Na^+$.

Still another embodiment relates to alkaline cells with zinc additive compounds of the formula (Ib)

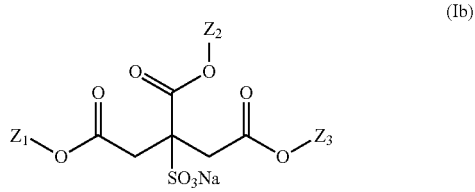

Preferred compounds of the formula (Ib) where $Z_1=Z_2=Z_3$ and all $Z_i$ are selected from $R_i(O(CH_2)_{ci})_{di}$—, where $c_i$=2, $d_i$=1-3, and $R_i$=$CF_3CF_2CH_2$— or $CF_3CF_2CF_2CH_2$—.

The compounds of the formulas I, Ia and formula Ib are referred to in the present invention as sulfotricarballylates and are based on esters of aconitic acid, onto the double bond of which a sulfonate group has been added. In particular, sulfotricarballylates containing three fluorinated end groups according to the invention are preferred. The compounds of the formula (I) according to the invention can also be in the form of mixtures, particularly also in the form of isomer mixtures (constitutional and/or configurational isomer mixtures). In particular, diastereomer and/or enantiomer mixtures are possible. Examples of sulfotricarballylates and their synthesis are disclosed in U.S. Patent Application Publication No. 2012/0111233 A1.

The sulfotricarballylate compounds of the formulas I, Ia and formula Ib containing more than one fluorinated end groups are preferred. The sulfotricarballylate compounds can have a molecular weight preferably between 800 and 1320, most preferably between 850 and 1000. The sulfotricarballylate compounds when added to an alkaline zinc electrode form a monolayer on the surface of the zinc the width of which can be estimated. It is preferred that this monolayer be as thin as possible so as to minimize polarization. Long chain surfactants because of their structure will have much thicker monolayers. Preferred monolayer thickness is less than 50 Angstroms, and it is most preferred to have a monolayer thickness less than 25 angstroms. Conversely, the minimum thickness of the layer must still be sufficient to impart the desired properties of the monolayer and, therefore, will be larger than 0.1 angstrom, and possibly even larger than 1, 5 and even 10 angstroms.

Barium sulfate has been added to alkaline batteries to provide a measure of increased conductivity in the cathode and to improve water/electrolyte distribution and management within the cathode. In an embodiment of the anode, barium sulfate can be added to the anode.

Functionalized barium sulfate is a form of barium sulfate in which a functional group, specifically a reactive organic compound, is associated with the surface of the barium sulfate. It is believed that adding functionality to barium sulfate will enable this additive to provide both water management and rheology modification in a single material. The functional group of the functionalized barium sulfate can form a bond with other polymers within the anode generating an octopus network to interlock organic and inorganic compounds. Barium sulfate can be functionalized at a nano-particulate level using various surface chemistry-altering techniques, so as to enable the selection of specific types of functional groups.

Sachtoperse AM and EP are available from Sachtleben Chemie GmbH. The difference between Sachtoperse AM and EP is the functional group—AM uses an amino group and EP uses an epoxide group. Sachtoperse was developed for the paint industry with the intent of enhancing corrosion resistance, chemical resistance, adhesion, anti-sagging, impact resistance, and flocculation stability. Other functional groups may be possible, whether used alone in various combinations, such as amines, alcohols, ethers, alkyl halides, thiols, aldehydes, ketones, esters, carboxylic acids, amides, nitriles, disulfides, imines, acid chlorides, anhydrides, nitro and/or thioethers.

Barium sulfate and/or functionalized barium sulfate can be added to the anode at a nominal concentration of 0.2 weight percent. Other concentrations are possible depending upon the type of functional group and its interactions with the other cell components, including 0.01 and 0.1 weight percent as potentially lower limits. Concentrations higher than 0.2 weight percent are also possible, although excessive amounts effectively occupy volume that could otherwise be dedicated to active materials.

A number of approaches have been proposed to screen zinc corrosion reduction additives. These include: a gel expansion test, a zinc gas generation test, measurement of anode impedance at both low and high frequency which provides information on the thickness and ion mobility associated with film formation on the surface of zinc, SEM images of zinc morphology, and whole cell performance and shelf characterization.

EXAMPLES

An anode formulation is created, optimized and tested. The formulation is assessed relative a control formulation in a series of performance experiments.

Example 1

Figure 2:
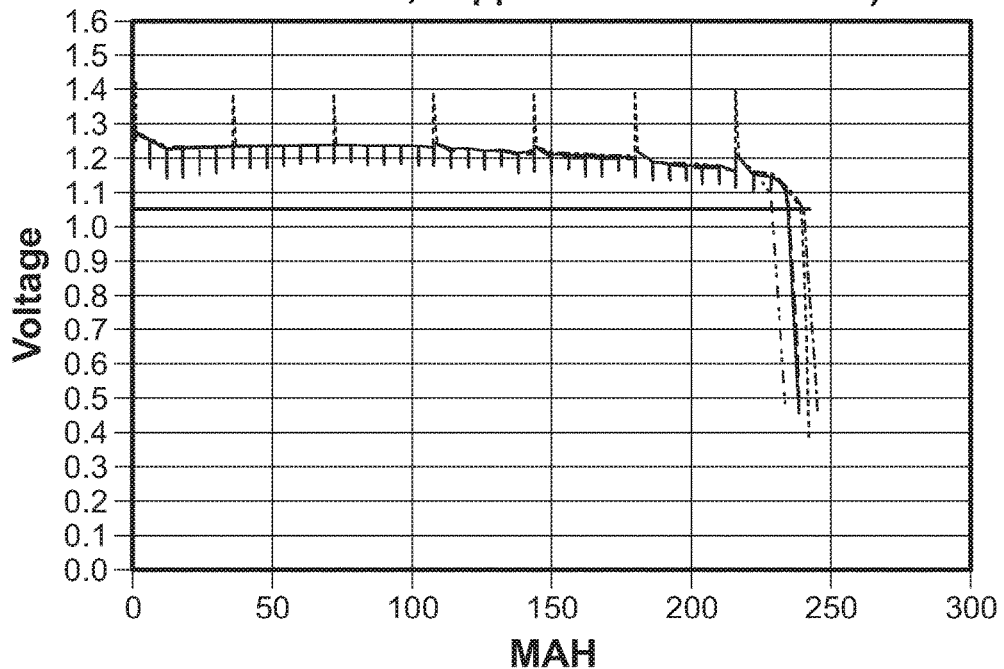
FIG. 2 is an illustration of the results of Example 1 showing the improved zinc input capacity while maintaining IEC performance.
Figure 2:
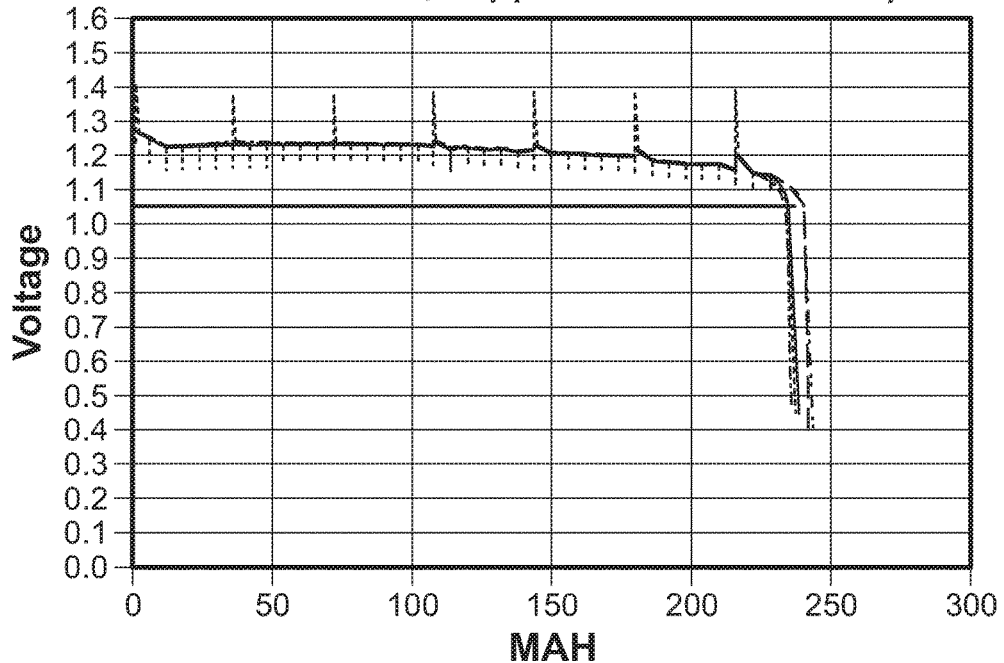

In order to determine if the zinc to electrolyte ratio could be increased without a detrimental impact on cell capacity, a comparative experiment was conducted. FIG. 2 shows the discharge profile for an anode formulation which includes Sachtoperse AM and sulfotricarballylate compound with a zinc to electrolyte ratio of 3.6 and 4.2.

These two cell constructions are similar with each containing 0.2 weight percent Sachtoperse AM and 80 ppm sulfotricarballylate. For the 3.6 ratio the zinc input was 278 mAh while the cell designed at a 4.2 ratio contained 298 mAh of anode capacity, achieved with less electrolyte.

While the results do not provide an obvious positive result for an increased Zn/El ratio the fact that negative results are not observed for the top metrics of HR-IEC to 1.05 volts and wireless to 1.1 volt is very encouraging as a pathway to enable the goal of increased input and delivered capacity. Performance of the control was 202 mAh on IEC and 133 mAh on wireless tests while the improved anode formulation provided 235 mAh and 171 mAh for these application tests. It appears from this experiment that changes in anode formulation are necessary to accommodate such an increased zinc capacity.

Example 2

In order to improve zinc utilization efficiency and thus improve the consumer metric of service on application, an anode additive which may improve ion mobility within the anode for increased zinc utilization was tested.

Two anode formulations were evaluated with functionalized barium sulfate and compared to a control formulation. These three anode formulations are described in Table 1.

TABLE 1

| | Formulation by Weight Percent | | |
|---|---|---|---|
| | Control 1st Graph | Sach AM 2nd Graph | Sach EP 3rd Graph |
| Zn | 99.71% | 99.27% | 99.27% |
| DK300 | 0.25% | 0.20% | 0.20% |
| InOH | 0.04% | 0.04% | 0.04% |
| ZnO | 0.00% | 0.25% | 0.25% |
| Sachtosperse EP | 0.00% | 0.00% | 0.25% |
| Sachtospere AM | 0.00% | 0.25% | 0.00% |

Figure 3:
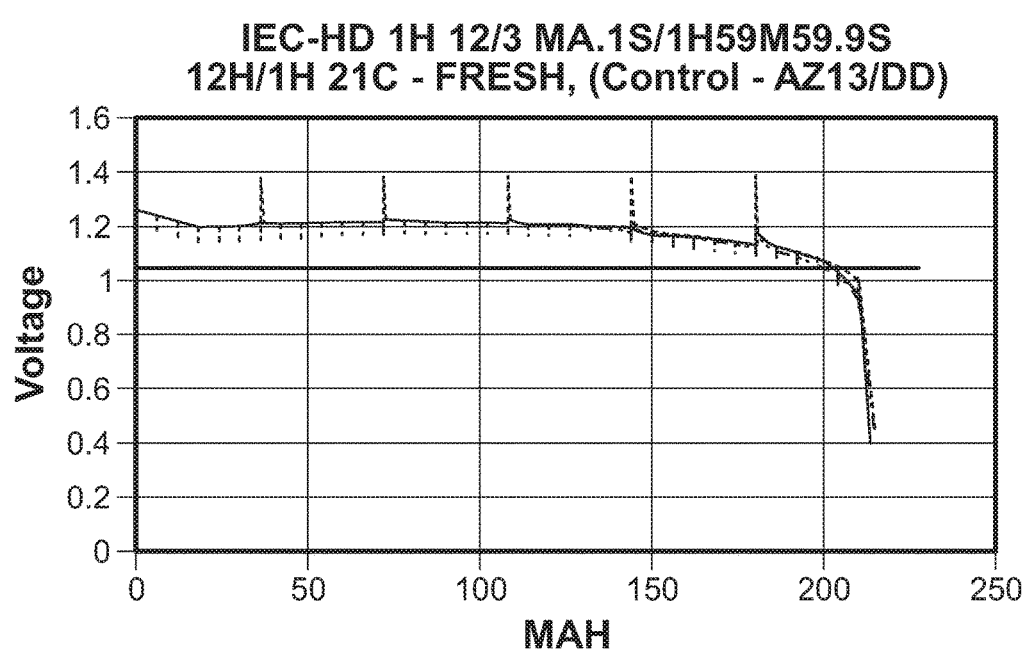
FIG. 3 is an illustration of the results of Example 2 showing Control discharge profile of a AZ13 cell.

FIG. 3 is the discharge profile of control AZ13 cell. Noted is the end of life failure mode of a sloping/declining operating voltage after about 150-170 mAh.

Figure 4:
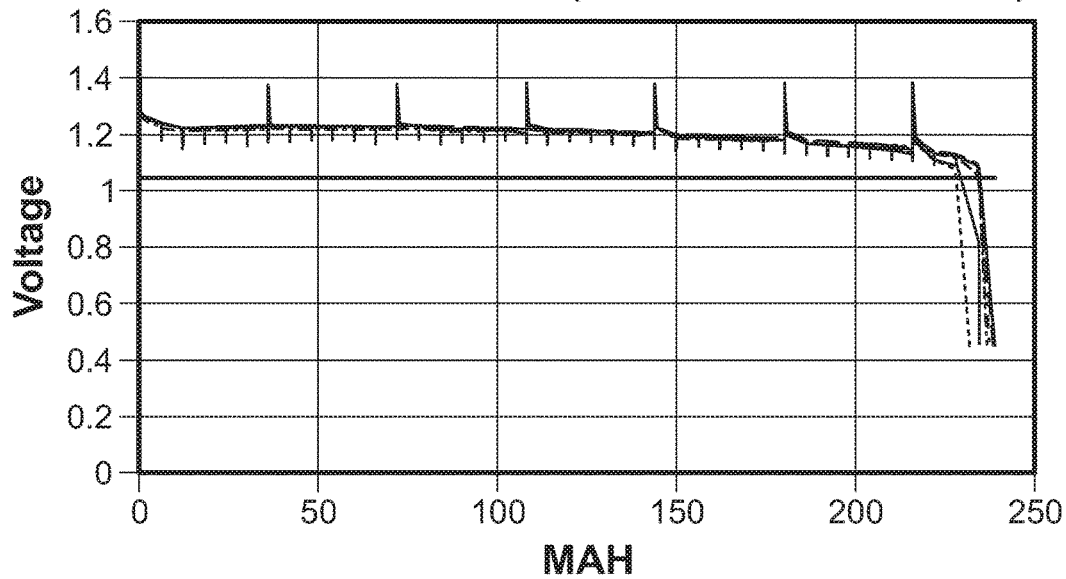
FIG. 4 is an illustration of the results of Example 2 showing Sachtoperse AM discharge profile of a AZ13 cell.
Figure 5:
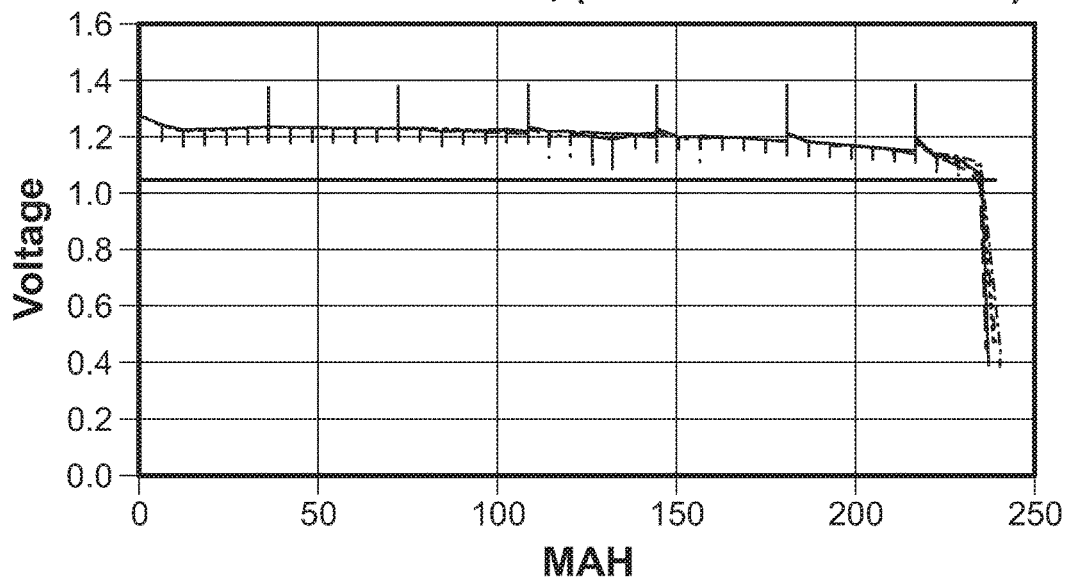
FIG. 5 is an illustration of the results of Example 2 showing Sachtoperse EP discharge profile of a AZ13 cell.

FIGS. 4 and 5 show the discharge profile for cells made with sulfotricarballylate surfactant, zinc oxide addition, and a very low 0.2 weight percent addition of functionalized barium sulfate in the anode dry blend. The discharge profiles in FIGS. 4 and 5 show that the sloping/declining operating voltage after about 150-170 mAh is eliminated. Instead both discharge profiles show a very sharp end of life which is both preferred and suggests a possible interaction between air electrode failures most likely from hydraulic flooding and water management within the anode.

Example 3

Based on the results from Experiment 2, an experiment was conducted to better define the interactions of: sulfotricarballylate surfactant, Sachtoperse AM, and the zinc to electrolyte ratio. These factors which had shown promising results were explored at three levels while zinc oxide and DV300K were held constant at 0.25% and 0.2% respectively. The zinc oxide was added to both help tie up electrolyte and to slow corrosion, gassing, and loss of capacity. The DV300K was added as a rheology aid.

Variables:

sulfotricarballylate (20, 50, and 80 ppm of zinc weight)

Sachtoperse AM (0, 0.1, and 0.2 weight percent)

Zn/El (3.6, 3.9, and 4.2)

This increase in ratio allowed the zinc input capacity to be increased from 278 to 289, and 298 mAh while maintaining the same void space within the anode compartment post discharge Specifically, the Anode formulation compositions and their associated discharge performance are show in Table 2.

TABLE 2

| Lot | Zn/El | Zn(mAh) | Tivida | ZnO | Sach | DK300 | InOH | IEC mAh(1.05 V) | Wireless mAh(1.1 V) |
|---|---|---|---|---|---|---|---|---|---|
| 1 | 3.6 | 278 | 0% | 0% | 0% | 0.25% | 0.04% | 205 | 133 |
| 9 | 3.9 | 289 | 50 ppm | 0.25% | 0.10% | 0.20% | 0.04% | 217 | 176 |
| 17 | 4.2 | 298 | 80 ppm | 0.25% | 0.20% | 0.20% | 0.04% | 237 | 185 |

Figure 6:
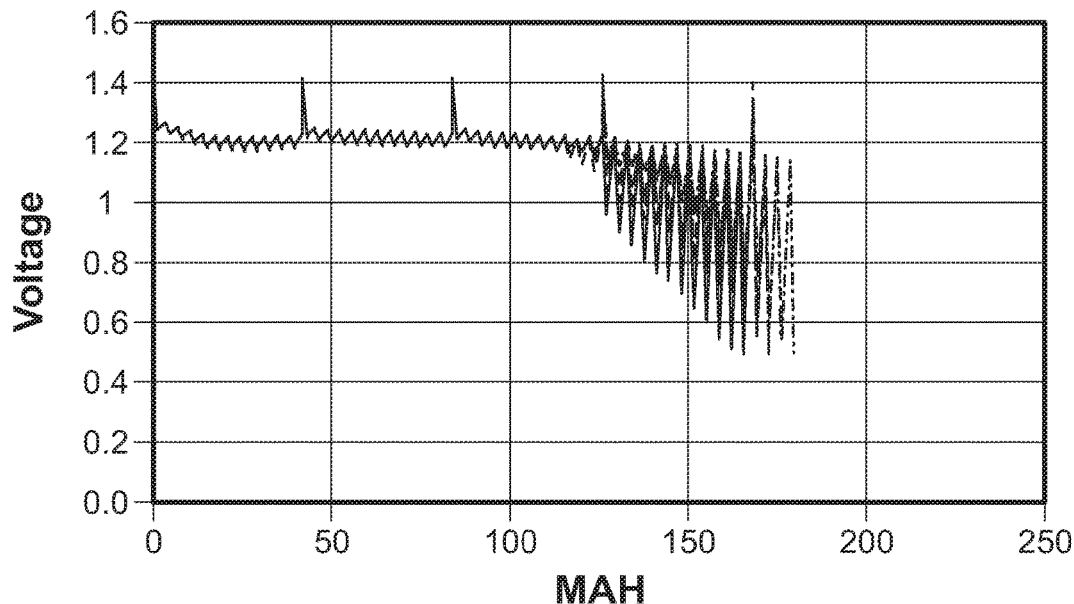
FIG. 6 is an illustration of the results of Example 3 showing comparative service of control to anode formulation changes.
Figure 6:
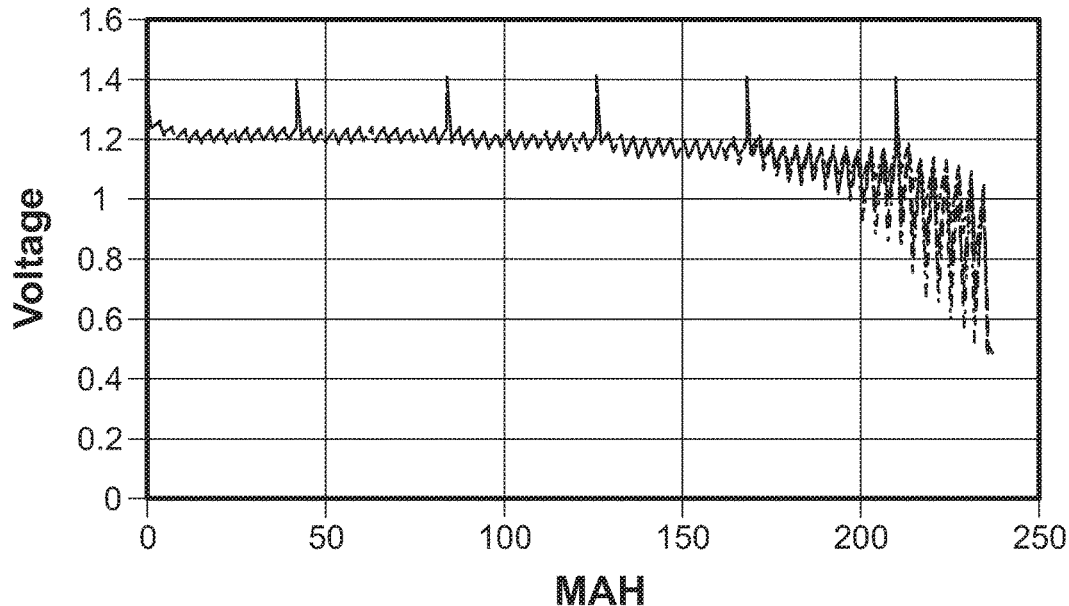

The graphs shown in FIG. 6 show improved results for the high rate and demanding wireless application tests (end of life is defined at 1.1 volt). Specifically, with an anode formulation of 50 ppm sulfotricarballylate, 0.1 Sachtoperse and a 3.9 Zn/El ratio, a goal of 175 mAh is exceeded. The results of this experiment also supported that product performance can be improved with the addition of Sachtoperse. IEC service of approximately 240 mAh was achieved at higher Zn/El ratios (about 3.80 to about 4.2) with at least 0.1% Sachtoperse AM.

These results are significant and confirm that it is possible: to add increased zinc input, without an associated inefficiency penalty; use a functionalized barium sulfate, and use a surfactant which is more robust in terms of concentration effects. Specifically, the Zn/Electrolyte can be increased without a negative response, with a ratio of 3.9-4.0 preferred, performance and end of life is improved with Sachtoperse, and there is an advantage to using sulfotricarballylate and the cell is insensitive to sulfotricarballylate concentration.

Example 4

An experiment was conducted to explore effects such as: zinc oxide addition, type of zinc oxide specifically nano versus standard zinc oxide particle size and surface area. In addition, Sachtoperse AM, Sachtoperse EP and non-functional barium sulfate were compared, and anode void volume and its impact on zinc efficiency was studied.

Figure 7:
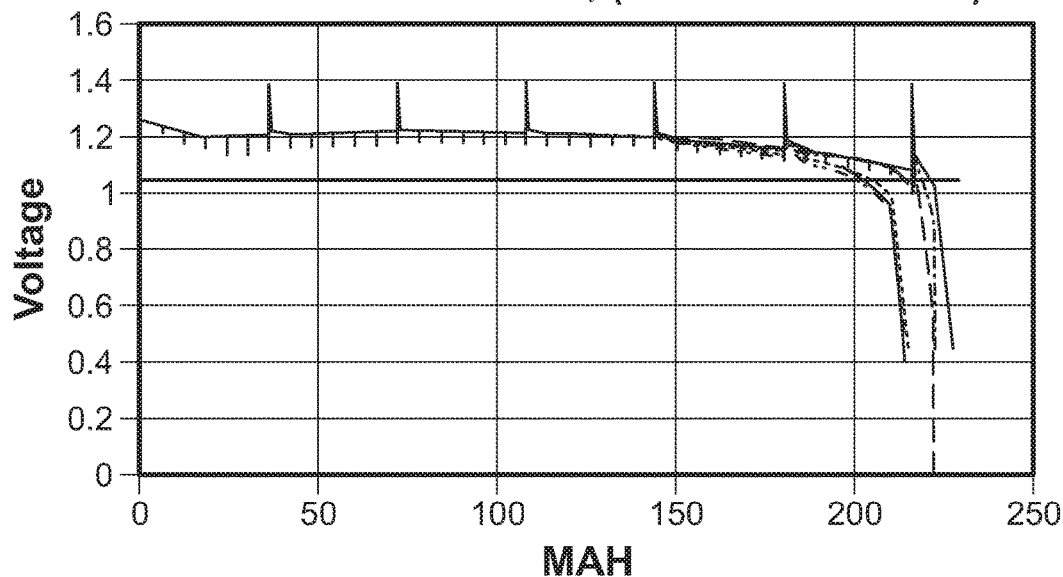
FIG. 7 is an illustration of the results of Example 4 showing the improved discharge profile of the anode formulation with nano zinc oxide relative the control.
Figure 7:
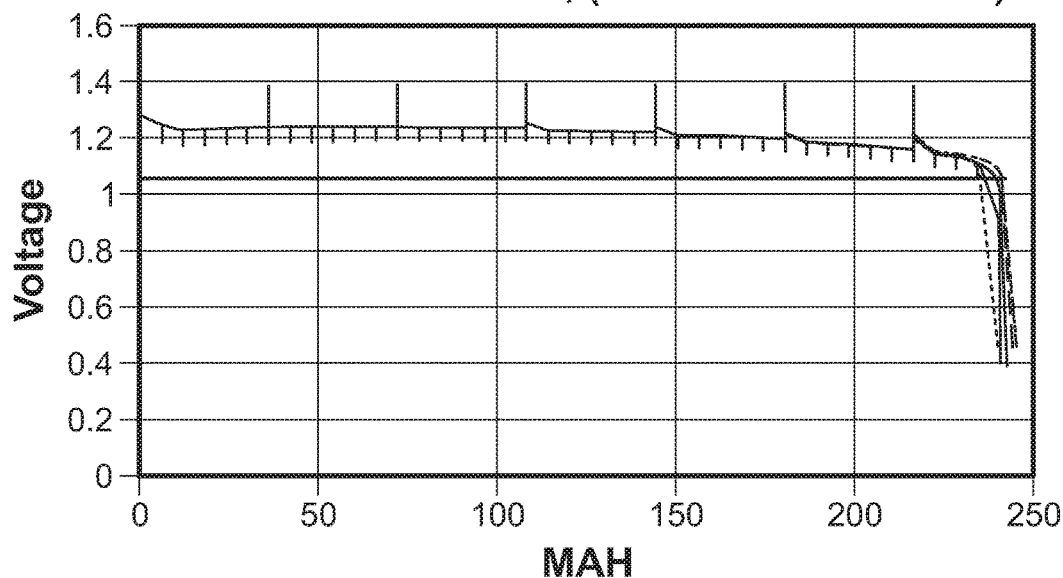

Results included the replication that both Sachtoperse AM and EP provide the desired performance. Barium sulfate without functional groups is also beneficial but without associated rheology benefits important to controlling anode mobility. Table 3 shows the details of the anode formulation relative the control formulation, and FIG. 7 shows the improved discharge profile of the anode formulation with nano zinc oxide relative the control. The nano zinc oxide used in this study was from Grillo and had a surface area of 29 square meters per gram.

TABLE 3

|  | Control | Improved |
|---|---|---|
| Zinc | 99.71% | 99.27% |
| Binder | 0.25% | 0.20% |
| InOH | 0.04% | 0.04% |
| nanoZnO | 0.00% | 0.25% |
| Sach AM | 0.00% | 0.25% |
| Tivida | 0 ppm | 80 ppm |
| Zn\El | 3.60 | 3.90 |

Figure 8:
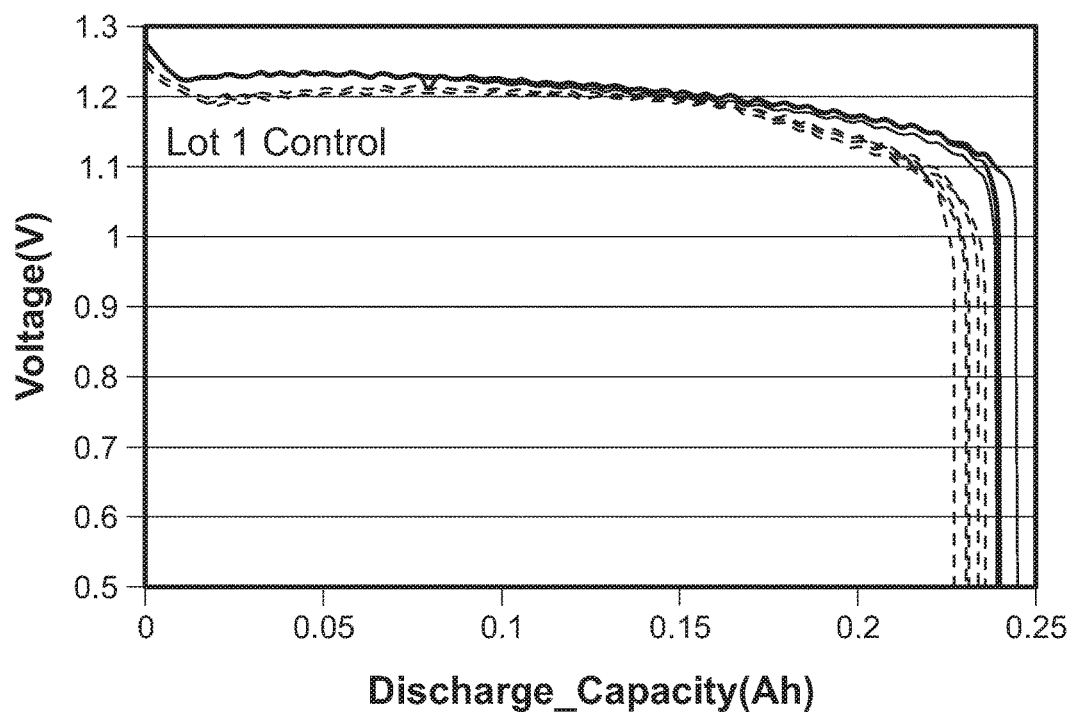
FIG. 8 is an illustration of the results of Example 4 showing improved operating voltage and end of life of the described anode formulation.

This experiment served as yet another replicate of the advantages of the recommended changes in the anode formulation; sulfotricarballylate, ZnO, and Sachtoperse. FIG. 8 shows that even on low rate applications—in this case a 3 mA continuous drain, improvements can be noted in a reduction in front end dip, improved operating voltage, improved run time, and improved end of life performance.

Figure 9:
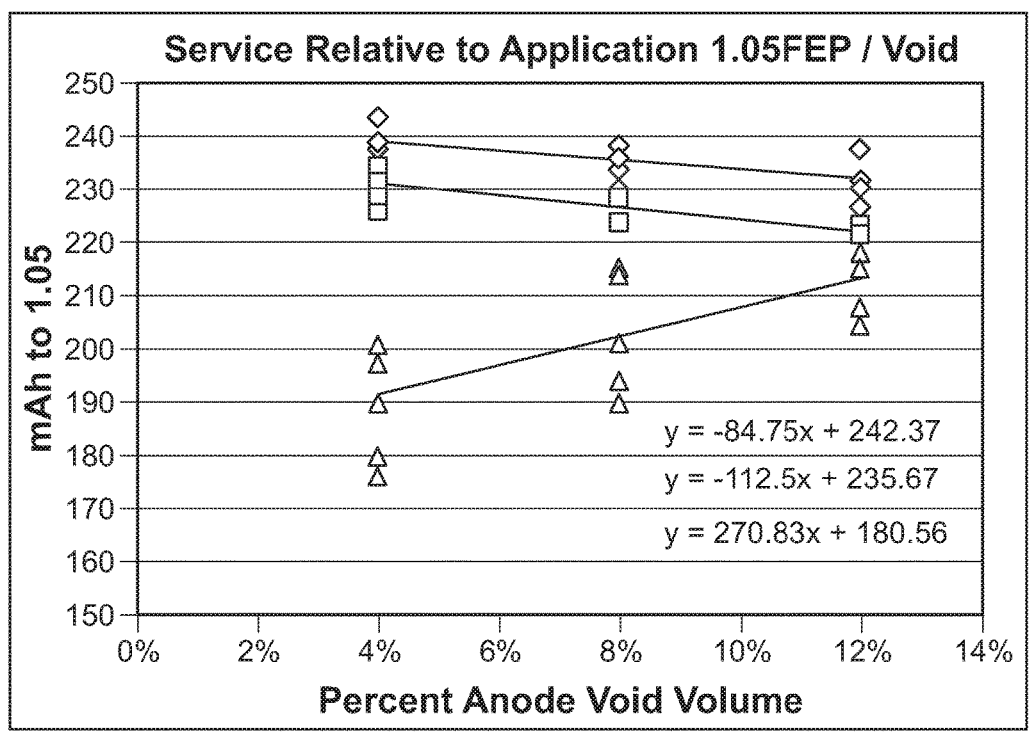
FIG. 9 is an illustration of the results of Example 4 showing performance as a function of application drain rate and anode void volume.

FIG. 9 illustrates that on high rate test such as wireless the amount of anode void does play a role in service delivered particularly to 1.05 volts. The upper line shown in blue represents service on 3 mA continuous, the next red line represents service on IEC hr, 3 mA background with 12 mA pulses, and the lower green line represents service on wireless testing in which 5 mA must be sustained for 15 minutes at a time, about the same as 5 mA continuous in terms of electrode demand. The two lower rate tests indicate that increasing void is not desirable, while the wireless test shows that increased void results in increased performance. This result requires that a different controlling mechanism is in place at high rate drain. It is additionally understood from this result that variations in the air electrode performance dominate at higher rates and contribute to increased variability. This variability was accommodated in the next example.

Example 5

Figure 10:
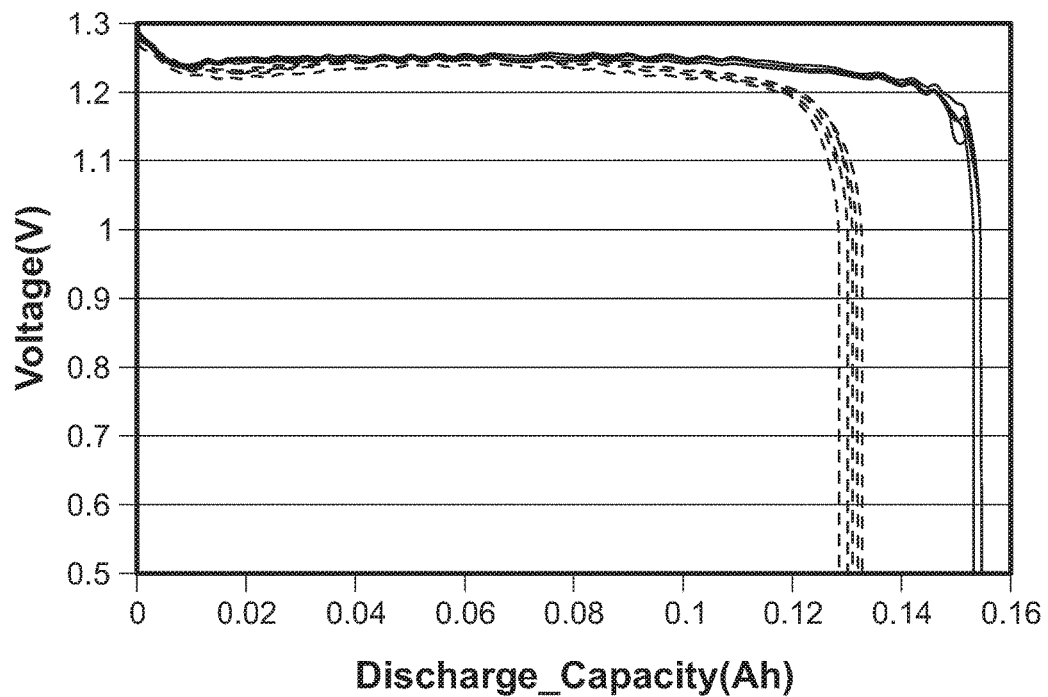
FIG. 10 is an illustration of the results of Example 5 showing control performance in black vs. a 312 cell's anode formulation on a 2 mA continuous discharge.
Figure 11:
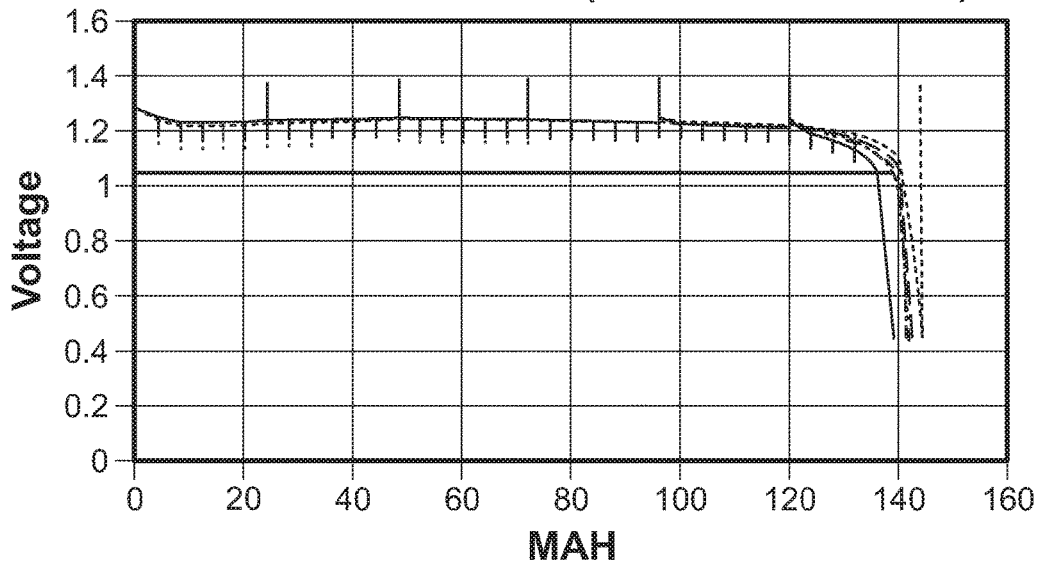
FIG. 11 is an illustration of the results of Example 5 showing control performance and the described anode formulation discharge profiles on IEC application testing.
Figure 11:
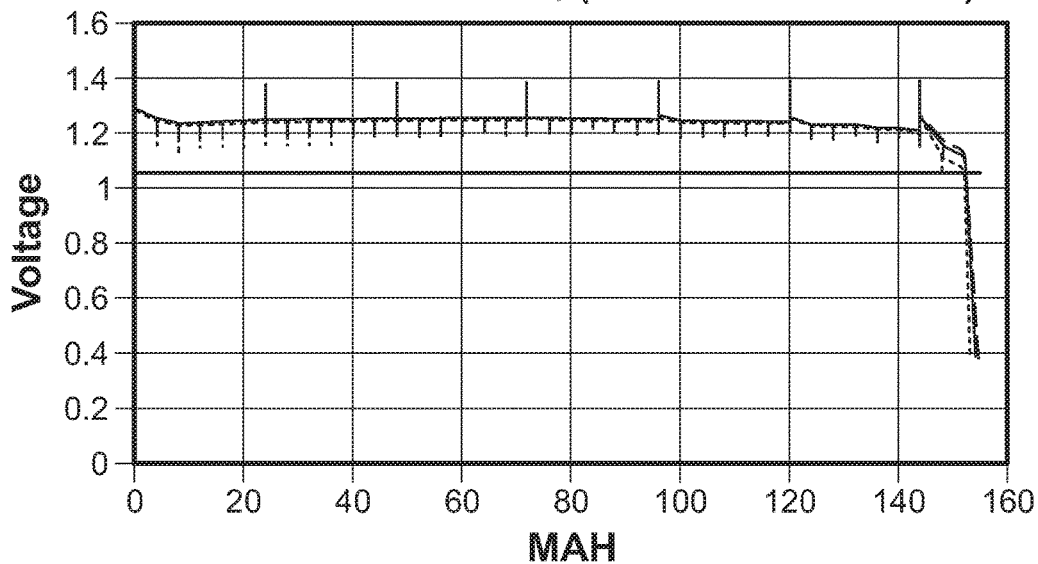

In this example the 312 size zinc air cell was used. The 312 zinc air cell basically uses the same diameter air electrode as the 13 size cell but demand on the electrodes is greatly reduced; about half the depth of discharge based on lower anode inputs and lower drain rates which equates to lower current densities on both electrodes. Table 4 shows the control and new anode formulation compositions. As would be expected the benefit of the anode formulation was only enhanced in the 312 cell. FIG. 10 shows the control performance in black vs. the 312 cell's anode formulation on a 2 mA continuous discharge. FIG. 11 shows the discharge profiles on IEC application testing. Similar to the AZ13 cell performance is significantly improved with the new anode formulation changes.

TABLE 4

|  | Control | Improved |
|---|---|---|
| Zinc | 99.71% | 99.30% |
| Binder | 0.25% | 0.20% |
| InOH | 0.04% | 0.04% |
| ZnO | 0.00% | 0.25% |
| Sach AM | 0.00% | 0.20% |
| Tivida | 0 ppm | 80 ppm |
| Zn\El | 3.60 | 4.00 |

The experiment results are consistent and support the conclusion that: sulfotricarballylate is effective in zinc corrosion control while improving cell impedance and providing robustness to concentration: the addition of zinc oxide is effective to limit the reaction of zinc to zinc oxide reaction products on shelf, and the use of functionalized barium sulfate provides for improved ion mobility, electrolyte/water management within the cell, and improved end of life operating voltage.

While the invention has been described in detail herein in accordance with certain preferred embodiments thereof, many modifications and changes therein may be affected by those skilled in the art without departing from the spirit of the invention. Accordingly, it is our intent to be limited only by the scope of the appending claims and not by way of the details and instrumentalities describing the embodiments shown herein.

What is claimed is:

1. An alkaline electrochemical cell, comprising:
a container; a negative electrode, a positive electrode, wherein said negative electrode and said positive electrode are disposed within the container, and an aqueous alkaline electrolyte, wherein the negative electrode comprises zinc and functionalized barium sulfate.

2. The cell according to claim 1, wherein the negative electrode further comprises a fluorosurfactant.

3. The cell according to claim 2, wherein said fluorosurfactant is a sulfotricarballylate.

4. The cell according to claim 2, wherein a formula for said fluorosurfactant is selected from (a) or (b):

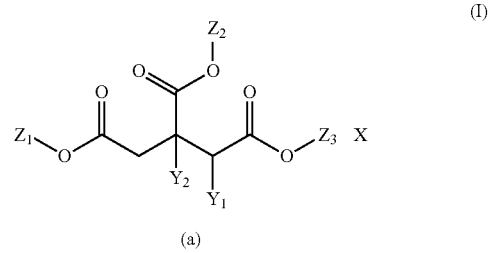

(a)

where the groups $Z_1$, $Z_2$, and $Z_3$ are, independently of one another, branched or unbranched alkyl groups or groups of the structure $R_i(A(CR_1R_2)_{ci}-(CR_3R_4)_{c'i})di-$, where the respective indices ci and c'i are, independently of one another, 0-10, and di=0-5, where $R_i$ is a branched or unbranched, fluorine-containing alkyl radical, $R_1$ to $R_4$ are, independently of one another, hydrogen or a branched or unbranched alkyl group, ci and c'i are not simultaneously 0, and A=O, S and/or N, $Y_1$ is an anionic polar group and $Y_2$ is a hydrogen atom, or vice versa, X is a cation, and at least one of the groups $Z_1$, $Z_2$, and $Z_3$ is a group of the structure $R_iA(CR_1R_2)_{ci}$—$(CR_3R_4)_{ci'}$)di-; and

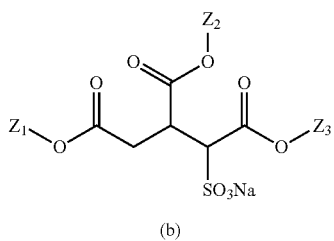

(Ia)

(b)

where $Z_1=Z_2=Z_3=F_3C(CF_2)(CH_2)(O(CH_2CHCH_2CH_3))$.

5. The cell according to claim 4, wherein the negative electrode further includes zinc oxide, and wherein said zinc oxide is nano-sized.

6. The cell according to claim 5, wherein each of $Z_1$, $Z_2$, and $Z_3$ comprises a fluorinated end group, and each of said fluorinated end groups comprises $F_3C(CF_2)_2$ or $F_3C(CF_2)$.

7. The cell according to claim 5, wherein each of $Z_1$, $Z_2$, and $Z_3$ comprises a fluorinated end group, and wherein said fluorinated end groups are identical.

8. The cell according to claim 5, wherein the functionalized barium sulfate comprises at least one of: an amino group and an epoxide group.

9. The cell according to claim 2, wherein said fluorosurfactant is

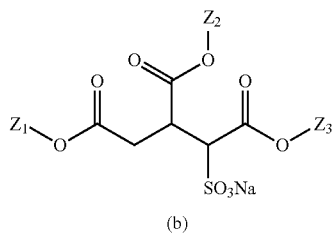

(ia)

(b)

where $Z_1=Z_2=Z_3=F_3C(CF_2)(CH_2)(O(CH_2CH_2CH_2CH_2))$.

10. The cell according to claim 1, wherein the positive electrode is an air electrode.

11. The cell according to claim 1, wherein the functionalized barium sulfate comprises at least one of: an amino group and an epoxide group.

12. The cell according to claim 1, wherein the functionalized barium sulfate is provided at a concentration of no greater than 0.2 weight percent of negative electrode mixture.

13. The cell according to claim 12, wherein the functionalized barium sulfate comprises a functional group selected from: an amino group, an epoxide group and combinations thereof.

14. The cell according to claim 1, wherein the negative electrode further includes zinc oxide, and wherein said zinc oxide is nano-sized.

15. The cell according to claim 14, wherein the functionalized barium sulfate comprises at least one of: an amino group and an epoxide group.

16. The cell according to claim 14, wherein the functionalized barium sulfate comprises an epoxide group.

17. The cell according to claim 1, wherein the weight ratio of zinc to electrolyte is greater than 3.6.

18. The cell according to claim 1, wherein the positive electrode comprises manganese dioxide.

* * * * *

UNITED STATES PATENT AND TRADEMARK OFFICE
CERTIFICATE OF CORRECTION

| | |
|---|---|
| PATENT NO. | : 10,319,991 B2 |
| APPLICATION NO. | : 15/521223 |
| DATED | : June 11, 2019 |
| INVENTOR(S) | : Marple |

Page 1 of 1

It is certified that error appears in the above-identified patent and that said Letters Patent is hereby corrected as shown below:

On the Title Page

Insert item (30), as follows:
--(30) Foreign Application Priority Data
October 7, 2015 (WO) PCT/US2015/054489--

Signed and Sealed this
Sixteenth Day of June, 2020

Andrei Iancu
*Director of the United States Patent and Trademark Office*